United States Patent [19]
Miyata et al.

[11] Patent Number: 5,897,819
[45] Date of Patent: Apr. 27, 1999

[54] PROCESS OF MAKING A GUIDE WIRE FOR A CATHETER

[75] Inventors: Naohiko Miyata; Masashi Momota; Minoru Saruta, all of Aichi-ken, Japan

[73] Assignee: Asahi Intecc Co., Ltd., Aichi-ken, Japan

[21] Appl. No.: 08/885,949

[22] Filed: Jun. 30, 1997

Related U.S. Application Data

[62] Division of application No. 08/744,316, Nov. 7, 1996.

[30] Foreign Application Priority Data

Jul. 10, 1996 [JP] Japan .................................... 8-181022

[51] Int. Cl.⁶ .................................................. B29C 47/06
[52] U.S. Cl. .......................... 264/103; 264/136; 264/137; 264/157; 264/171.15; 264/171.16; 264/171.2; 264/230; 264/322; 264/325; 427/358; 427/421
[58] Field of Search .................................... 264/103, 136, 264/137, 157, 171.15, 171.16, 171.2, 230, 322, 325; 427/358, 421

[56] References Cited

U.S. PATENT DOCUMENTS

| | | |
|---|---|---|
| 4,579,127 | 4/1986 | Haacke . |
| 4,682,607 | 7/1987 | Vaillancourt et al. . |
| 5,217,026 | 6/1993 | Stoy et al. . |
| 5,433,200 | 7/1995 | Fleischhacker, Jr. . |
| 5,498,250 | 3/1996 | Prather . |

FOREIGN PATENT DOCUMENTS

| | | |
|---|---|---|
| 200 919 A1 | 11/1986 | European Pat. Off. . |
| 480 427 A1 | 4/1992 | European Pat. Off. . |
| 4-20453 | 5/1992 | Japan . |

*Primary Examiner*—Leo B. Tentoni
*Attorney, Agent, or Firm*—Sughrue, Mion, Zinn, Macpeak & Seas, PLLC

[57] ABSTRACT

In a guide wire is for a catheter, a core wire prepared by twisting a plurality of thin threads in which a leading end of the core wire is diametrically reduced to be a thinnest tip. A resin layer is coated on an outer surface of the core wire. The thinnest tip is treated by tightly uniting together a twisted ends of the thinnest threads.

3 Claims, 6 Drawing Sheets

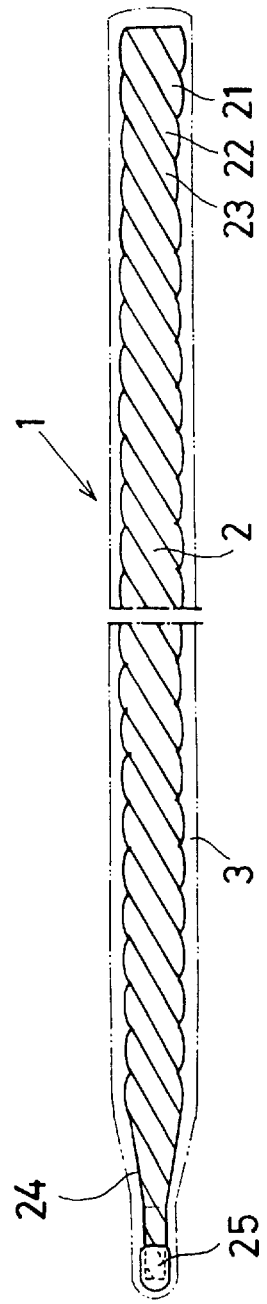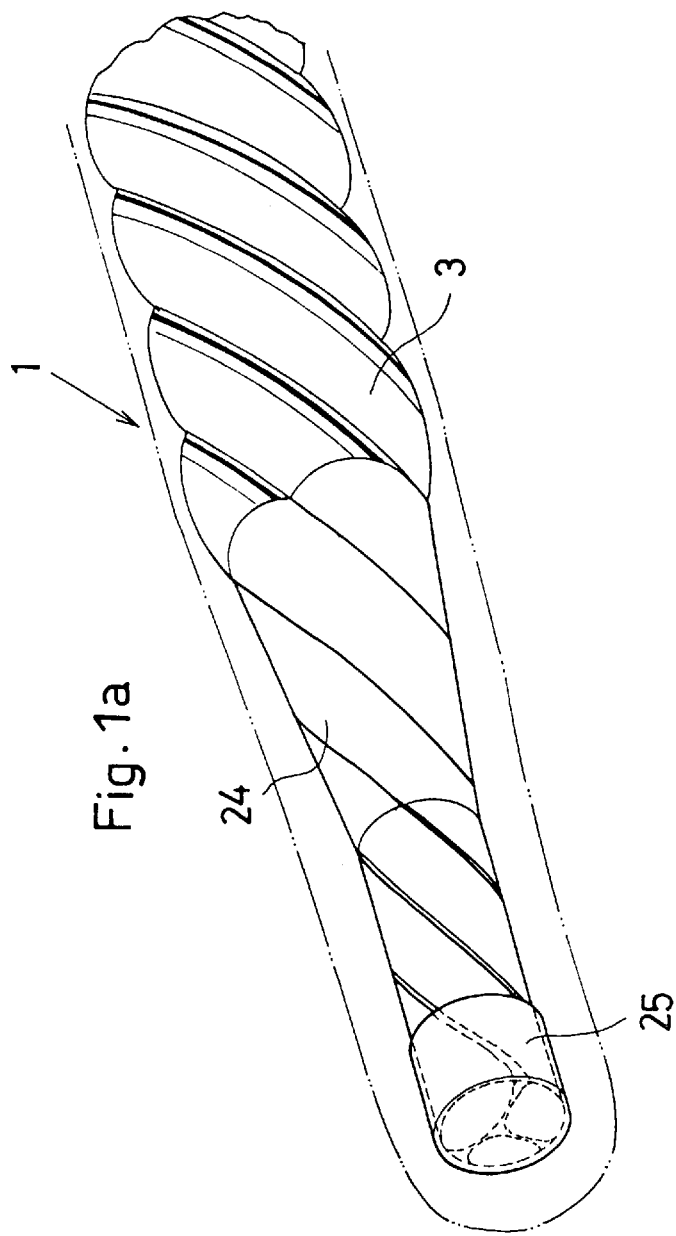

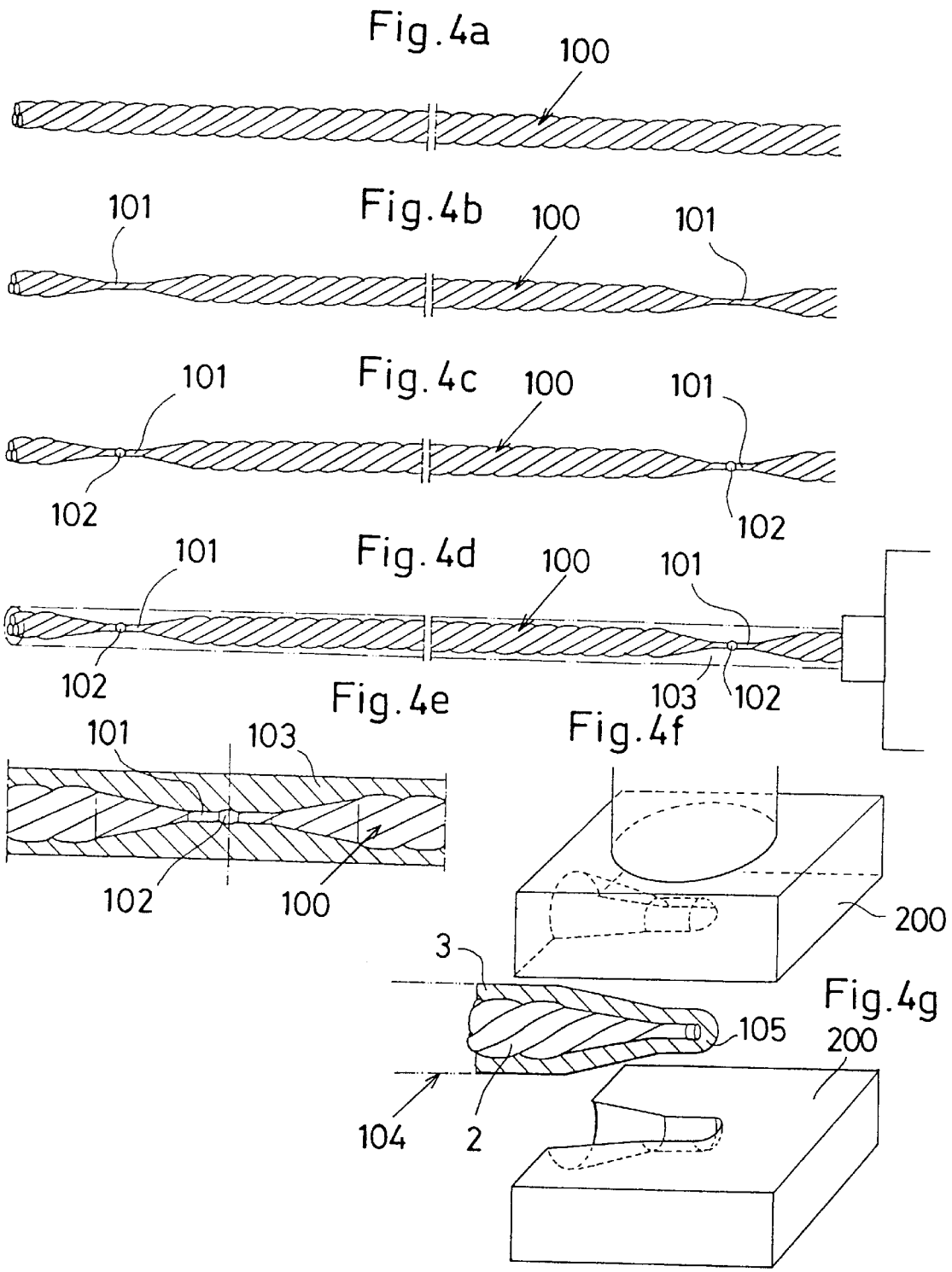

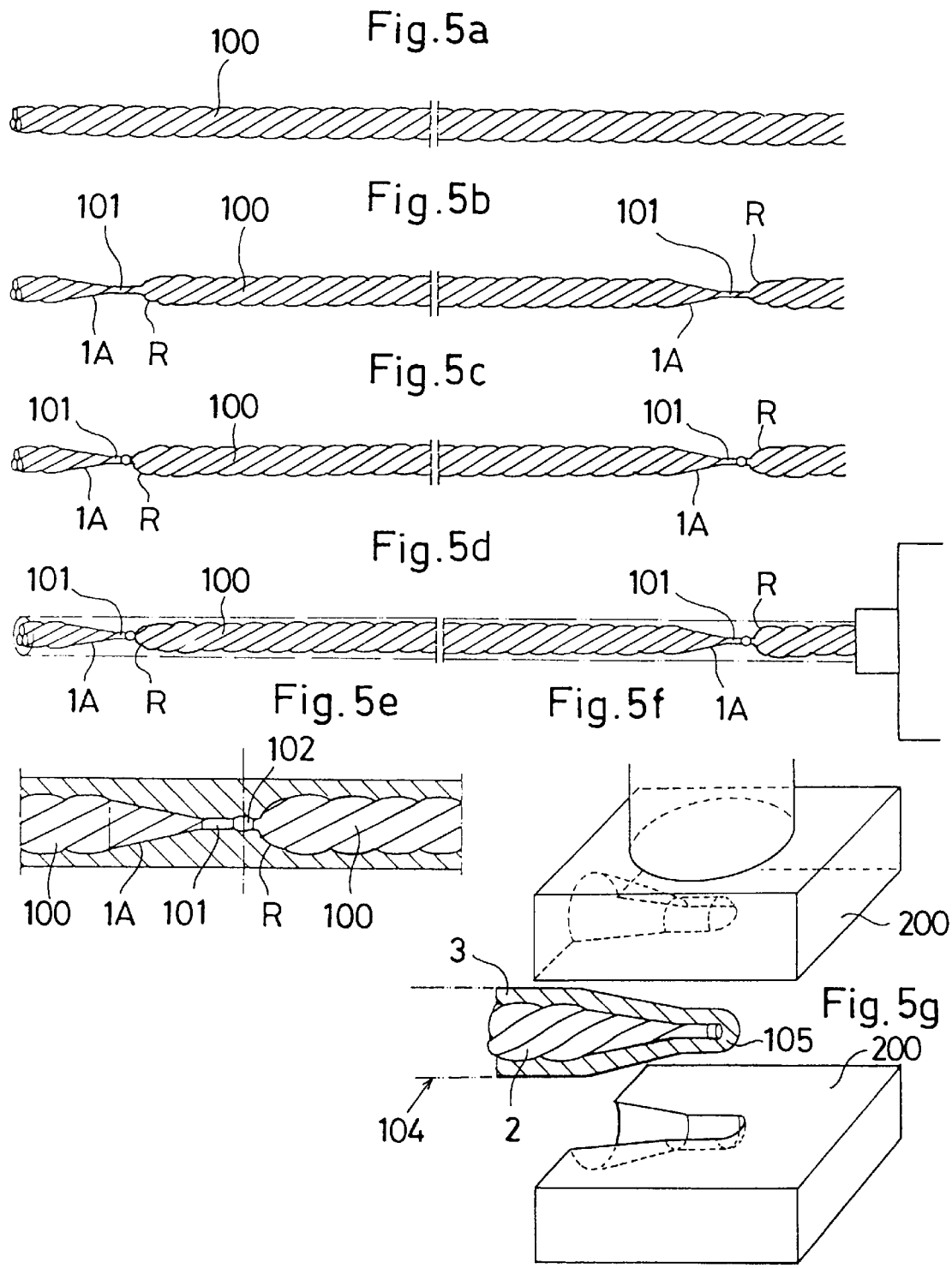

PROCESS OF MAKING A GUIDE WIRE FOR A CATHETER

This is a Division of application Ser. No. 08/744,316 filed Nov. 7, 1996.

BACKGROUND OF THE INVENTION

1. Field of the Invention

This invention relates to a medical guide wire which is to be penetrated into a somatic body to guide a catheter prior to inserting the catheter.

2. Description of the Related Art

Upon inserting the catheter to a body so as to inject a contrast medium into an affected part, a metallic guide wire is used which extends by approx. 20 mm from a leading end of the catheter. After reaching the affected area, the guide wire is withdrawn with the catheter remaining at the affected area, and then the contrast medium is injected through the catheter into the affected area.

As this type of guide wire, there is provided a wire device disclosed by Japanese Patent Publication No. 4-20453. In the reference of Japanese Patent Publication No. 4-20453, a core wire is made by a plurality of thin threads, and a leading end of the core wire is constricted to form a thinned tip. On an entire surface of the core wire, a resin layer is coated. Both ends of the guide wire are crooked to flexibly move so that the guide wire can be smoothly inserted into a complicated and entangled vascular system.

However, it is feared that the thinned end of the twisted threads will become loose when treating the body with the thinned end, when the twisted threads are coated with a resin layer on the outer surface of the core wire. With the frequent use of the guide wire, the leading end of the thin threads tends to become unraveled so that the thin threads break the resin layer to expose the thin treads outside the resin layer so as to do harm on the somatic tissue system. This restricts the flexing turns and degree of the leading end of the guide wire. Moreover, the crooked end of the guide wire tends to be unidirectionally oriented so as to deteriorate its maneuverability.

Therefore, it is an object of the invention to provide a guide wire which is capable of effectively preventing the twisted end from inadvertenly becoming loose.

It is another object of the invention to provide a guide wire which is capable of improving a manipulability when encountering a bifurcating point of a vascular system.

It is yet another object of the invention to provide a method of efficiently making a guide wire.

SUMMARY OF THE INVENTION

According to the invention, there is provided a guide wire comprising: a core wire prepared by twisting a plurality of thin threads, a leading end of the core wire being diametrically reduced to be a thinnest tip; a resin layer coated on an outer surface of the core wire; and the thinnest tip being treated by tightly bonding together twisted ends of the thinnest threads.

At the time of bonding the twisted ends of the thinnest threads, the bonding procedure may be done by means of soldering, resistance welding, laser beam welding, shield-arc welding or the like. By flattening the leading end of the thinned end, it is possible to improve its maneuverability. It is preferable to make the core wire by entwisting three or four stainless steel threads to secure a good rigidity, protecting against deformation and insuring a good resistance against repeated crooking actions.

Further, according to the invention, there is provided a method of making a guide wire comprising the steps of: preparing thinnest portions of a core wire which is made by twisting a plurality of thin threads; tightly uniting the thin threads of the thinnest portions; coating a resin layer on the core wire including the thinnest portions while extruding the core wire; severing a middle portion of the thinnest portions and cutting a middle portion of the core wire between the thinnest portions; and coating a resin layer on a severed end surface of the thinnest portions and a cutting end surface of the core wire by means of a hot pressing procedure. These procedures make it possible to efficiently manufacture the guide wire with a relatively low cost.

In brief, with the thin threads of the leading end thermally bonded together, it is possible to ensure a good resistance against the repeated crooking operation, and at the same time, positively preventing the thin threads of the leading end from inadvertently becoming unraveled even with the frequent use of its leading end. It is also possible to freely flex the leading end of the guide wire with a considerable degree of safety ensured.

By flattening the leading end of the guide wire, it is possible to orient the leading end toward the desired direction by whirling its leading end due to a rotating operation of a grip of the guide wire, when encountering the bifurcating point of the vascular system.

These and other objects and advantages of the invention will be apparent upon reference to the following specification, attendant claims and drawings.

BRIEF DESCRIPTION OF THE DRAWINGS

FIG. 1a is a plan view of a guide wire according to an embodiment of the invention;

FIG. 1b is a perspective view of a main part of the guide wire;

FIGS. 4a through 4g are sequential views showing how to manufacture the guide wire; and FIGS. 5a through 5g are sequential views showing how to manufacture the guide wire according to other embodiment of the invention.

DESCRIPTION OF THE PREFERRED EMBODIMENTS OF THE INVENTION

Figure 2A:
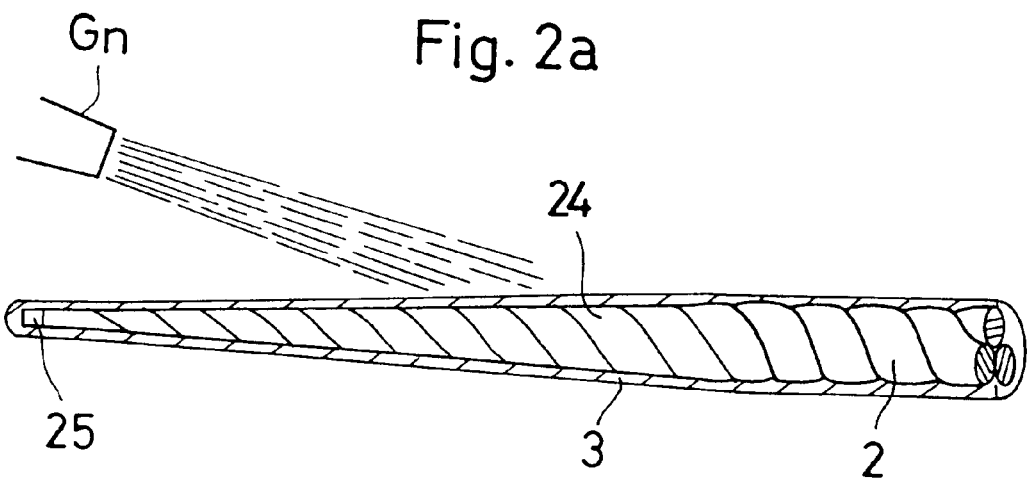
FIGS. 2a and 2b are sequential views of coating a resin layer on a core wire.

Referring to FIGS. 1a and 1b, a guide wire 1 has a metallic core wire 2 which is made by twisting a plurality of thin threads 21, 22, 23. On an entire surface of the core wire 2, a resin layer 3 is coated. The core wire 2 measures 0.43 mm in diameter, and a leading end of the core wire 2 is diametrically reduced progressively to form a tapered-off section 24. A distal end of the tapered-off section 24 provides a thinnest neck portion to form a thinned tip 25. At the thinned tip 25 of the leading end, a twisted end of the thin threads 21, 22, 23 is tightly united and thermally bonded by means of soldering, resistance welding, laser beam welding, shield-arc welding or the like.

Each of the thin threads 21, 22, 23 is made of a stainless steel which measures 0.25 mm in diameter, and twisted at a pitch of 3.9 mm. The tapered-off section 24 of the leading end is made by grinding or polishing to measure 100 mm in length. The stainless steel is selected as AISI304 whose diameter is preferably 0.20~0.40 mm. The twisiting pitch may be 2~8 mm. When the core wire 2 is made from four thin threads, ⌀0.2 mm stainless threads are twisted at the pitch of 3.9 mm.

Figure 2B:
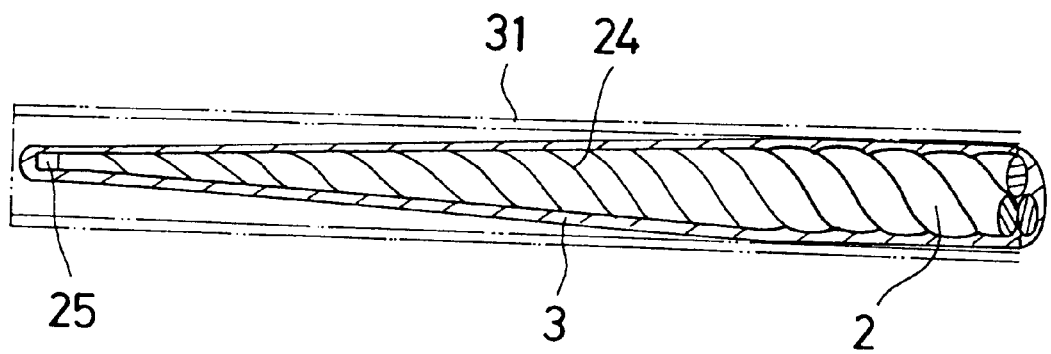

For the resin layer 3, polyurethane, polyamide or PTFE is used. As shown by FIG. 2a, the resin layer 3 is directly applied or sprayed on the core wire 2 by means of e.g., a spray gun (Gn). The resin layer 3 may be formed by providing a thermo-shrink tube 31 around the core wire 2 and thermally treating it at 400~450° C. as shown by FIG. 2b. Further, the resin layer 3 may be concurrently formed at the time of extruding the core wire 2 as described hereinafter.

According to the present invention, the twisted threads are thermally bonded at the thinned tip 25 of the tapered-off section 24 of the leading end. This makes it possible to freely bend the tapered-off section 24 with no bending tendency towards a specified orientation. This permits a repeated turns of beding the tapered-off section 24 to remarkably contribute to an extended service life. It is possible to insure a safety with no incident that the twisted thread end of the thinned tip 25 becomes loose to break into the resin layer 3 so as to expose it to the outside.

Figure 3:
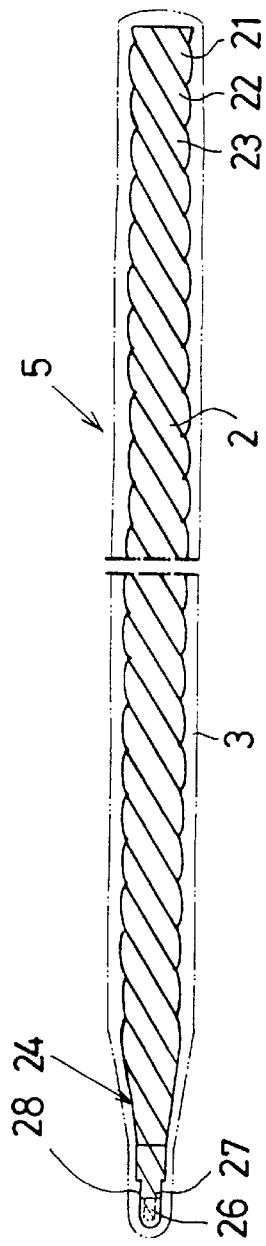
FIG. 3a is a plan view of a guide wire according to another embodiment of the invention.
FIG. 3b is a perspective view of a main part of the guide wire.
FIG. 3c is a perspective view of a main part of the wire guide according to a modification form of the invention.
Figure 3A:
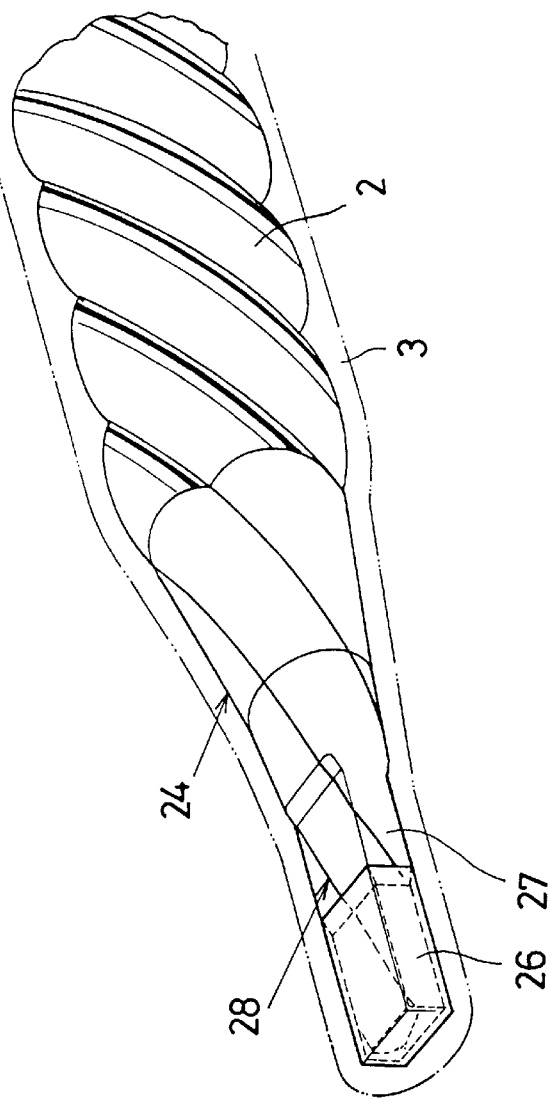
Figure 3B:
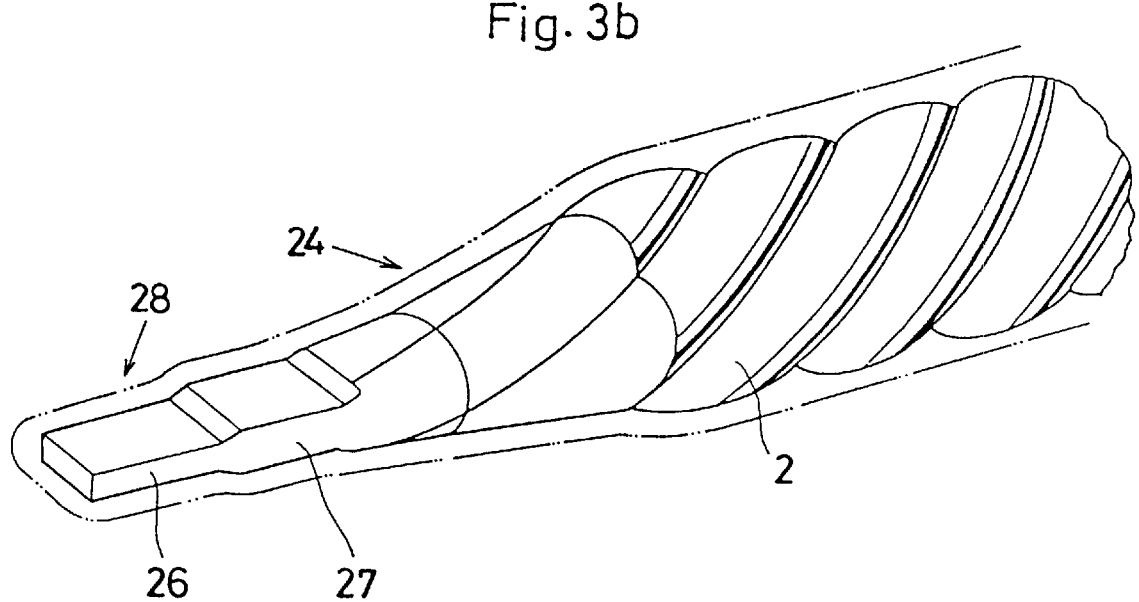

FIGS. 3a and 3b show a guide wire 5 according to another embodiment of the invention in which the thinned tip 25 of the tapered-off section 24 is squelched by means of a pressing procedure to form it into a flat-shaped configuration as designated by numeral 28. The flat portion 28 has a near distal end side flat section 26 (at the thinned tip 25) and a far distal end side flat section 27 (adjacent to the near distal end side flat section), each of which is in the form of a paralelopipedon. In this embodiment of the invention, it is possible to positively orient the thinned tip 25 of the guide wire 5 toward the desired direction by eccentrically whirling its flat portion 28 due to a rotating operation of a grip of the guide wire 5, when encountering the bifurcating point of the vascular system of our body. This insures a good maneuverability with a relatively easy manipulation.

In this instance, the flat portion 28 may be shaped into a multiple step type structure in which the thickness of the flat portion 28 progressively reduces by three steps or more as approaching the distal end of the guide wire 5 as shown in FIG. 3c. Upon considering the safety, it is necessary to secure the thickness of 0.095 mm or more for the topmost end of flat portion 28. Further, it is noted that a flat portion 28 may be bent in a zigzag manner along an axis to give the far distal end side flat section 27 a level higher than the near distal end side flat section 26 with respect to the axis.

On the contrary, in the guide wire 1 of FIG. 1a, the thinned tip 25 of the tapered-off section 24 is shaped into a columnar configuration. This leads to turning the thinned tip 25 around its axis without eccentrically whirling the thinned tip 25 when rotating the grip of the guide wire 1. This makes it rather difficult to orient the thinned tip 25 in the desired direction when manipulating the guide wire 1.

FIGS. 4a through 4g show a method of making the guide wire.
(i) An elongated wire 100 is prepared by twisting thin threads, and then severed by the length of approx. 3500 mm as shown by FIG. 4a.
(ii) As shown by FIG. 4b, a leading end portion is ground or milled to form a thinned portion 101.
(iii) Thereafter, the thin threads of the thinned portion 101 are tightly bonded to form a bonded section 102 by means of caulking or soldering as shown by FIG. 4c.
(iv) Then, the wire 100 is extruded with the resin to form a resin layer 103 coating on the wire 100 as shown by FIG. 4d.
(v) The layer coating wire 104 (hereinafter) is cut at a middle of the bonded section 102 as shown by FIG. 4e.
(vi) With the use of a hot press machine 200, the resin layer 103 is melted at a cutting end of the layer coating wire 104 so as to form a semi-spherical head 105 which coats a leading end surface of the core wire 2 as shown by FIGS. 4f and 4g.
(vii) When additionally forming the flat portion 28, a step of squelching the thinned portion 101 to flatten the portion 101 is provided between the steps (ii) and (iii).

With the use of the method of making the guide wire 1 (5), it is possible to mass produce it with a relatively low cost.

FIGS. 5f and 5g show another embodiment of the invention in which the tapered-off section 1A has only one end of the twisted wire 100, and the other end is formed into a semi-spherical configuration as designated by R. The thinned portion 101 is severed at the thermally bonded portion as designated by 102.

It is noted that an angular degree of the tapered-off section 24 can be determined as desired, and a diameter of the thinned tip 25 measures from 0.10 mm to 0.30 mm, and a thickness of the synthetic resin 103 ranges from 0.12 mm to 0.33 mm.

While the invention has been described with reference to the specific embodiments, it is understood that this description is not to be construed in a limiting sense in as much as various modifications and additions to the specific embodiments may be made by skilled artisan without departing the spirit and scope of the invention.

What is claimed is:

1. A method of making a guide wire comprising the steps of:
   twisting a plurality of thin threads to form a core wire;
   preparing thinnest portions of the core wire;
   tightly uniting thin threads of the thinnest portions of the core wire;
   extruding the core wire with a resin to form a resin layer on the core wire including the thinnest portions;
   severing a middle portion of the thinnest portions of the core wire between the thinnest portions; and
   melting and reshaping the resin layer on a severed end surface of the middle portion of the thinnest portions of the core wire by means of a hot pressing procedure.

2. A method of making a guide wire comprising the steps of:
   twisting a plurality of thin threads to form a core wire;
   preparing thinnest portions of the core wire;
   tightly uniting thin threads of the thinnest portions of the core wire;
   extruding the core wire with a resin to form a resin layer on the core wire including the thinnest portions;
   severing a portion of the tightly united thinnest portions; and
   melting and reshaping the resin layer on a severed end surface of the severed portion of the thinnest portions of the core wire by means of a hot pressing procedure.

3. A method of making a guide wire as recited in claim 2 further comprising the step of: squelching the thinnest portions of the core wire into a flat-shaped configuration concurrently at the time when preparing the thinnest portions of the core wire.

* * * * *